United States Patent [19]

Okabe et al.

[11] 4,451,401
[45] May 29, 1984

[54] ANTIBIOTICS AND PROCESS FOR PRODUCTION THEREOF

[75] Inventors: Mitsuyasu Okabe, Fujisawa; Takeo Yoshioka, Ayase; Yasuo Fukagawa, Kamakura; Rokuro Okamoto, Fujisawa; Kageaki Kouno, Tokyo; Tomoyuki Ishikura, Chigasaki, all of Japan

[73] Assignee: Sanraku-Ocean Co., Ltd., Tokyo, Japan

[21] Appl. No.: 394,166

[22] Filed: Jul. 1, 1982

[30] Foreign Application Priority Data

Jul. 1, 1981 [JP] Japan ................................ 56-101162
Feb. 4, 1982 [JP] Japan .................................. 57-15490

[51] Int. Cl.³ .......................................... C07D 487/04
[52] U.S. Cl. .............................. 260/245.2 T; 435/119; 424/274
[58] Field of Search .................................. 260/245.2 T Primary Examiner—Mary C. Lee
Attorney, Agent, or Firm—Wenderoth, Lind & Ponack

[57] ABSTRACT

A compound represented by the following formula

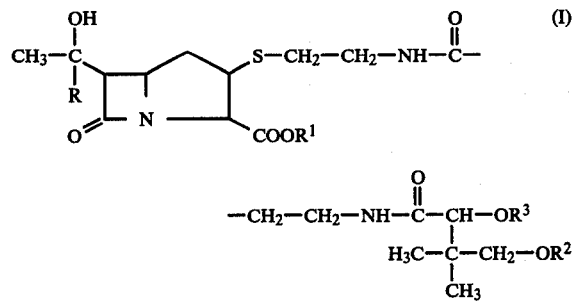

wherein
R represents a hydrogen atom or a methyl group,
$R^1$ represents a hydrogen atom or an ester residue, and
$R^2$ and $R^3$ represent hydrogen atoms respectively, or taken together, a group of the formula

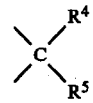

in which each of $R^4$ and $R^5$ represents a hydrogen atom, a lower alkyl group or a phenyl group, and its salt; and a process for the production thereof.

7 Claims, No Drawings

ANTIBIOTICS AND PROCESS FOR PRODUCTION THEREOF

This invention relates to novel antibiotics and a process for their production. More particularly, it relates to carbapenem compounds of the following formula

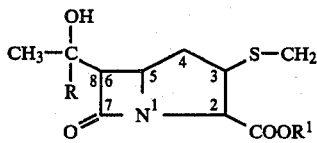

wherein R represents a hydrogen atom or a methyl group, $R^1$ represents a hydrogen atom or an ester residue, and $R^2$ and $R^3$ represent hydrogen atoms, respectively, or taken together, a group of the formula

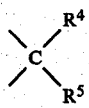

in which each of $R^4$ and $R^5$ represents a hydrogen atom, a lower alkyl group or a phenyl group, and salts thereof, and to a process for their production.

Antibiotics having a 7-oxo-1-azabicyclo[3.2.0]hept-2-ene-2-carboxylic acid skeleton of the formula

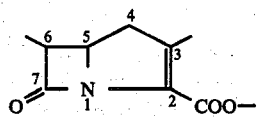

generally have high antimicrobial activity and β-lactamase-inhibitory property. Various 7-oxo-1-azabicyclo[3.2.0]hept-2-ene-2-carboxylic derivatives or carbapenem compounds have heretofore been produced by fermentative, semisynthetic and wholly synthetic methods. These antibiotic substances include, for example, thienamycin [Journal of Antibiotics, Vol. 32, pages 1 to 12 (1979)]; epithienamycins [Abstracts 80 and 31 of the 17th Interscience Conference on Antimicrobial Agents and Chemotherapy (1977)]; N-acetylthienamycin [West German Pat. No. 2652681 (1977)]; olivanates [Journal of Antibiotics, Vol. 32, pages 287 to 304 (1979)]; PS-5 [Journal of Antibiotics, Vol. 32, pages 262 to 286 (1979)]; PS-6 and PS-7 [Journal of Antibiotics, Vol. 33, pages 1128 to 1137 (1980)]; No. $17927A_1$ substance and No. $17927A_2$ substance (Japanese Laid-Open Patent Publications Nos. 103401/1978 and 109997/1978); KA-6643-A substance (Japanese Laid-Open Patent Publication No. 139280/1980); and various carbapenem antibiotics obtained by wholly synthetic methods (e.g. Japanese Laid-Open Patent Publication No. 5478/1981).

The KA-6643-A substance is a carbapenem antibiotic of the following formula:

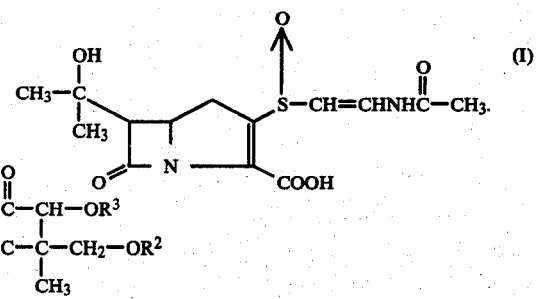

The No. $17927A_1$ and $17927A_2$ substances are antibiotics represented by the following formulae respectively:

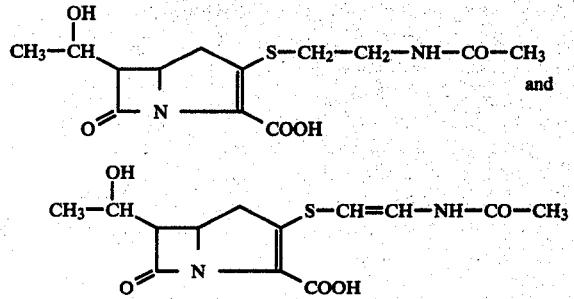

Continued investigation of fermentation conditions for carbapenem-producing microorganisms recently led to the discovery of No. 17927D substance (2,3-dihydro compound of the following formula) (Japanese Laid-Open Patent Publication No. 24129/1980).

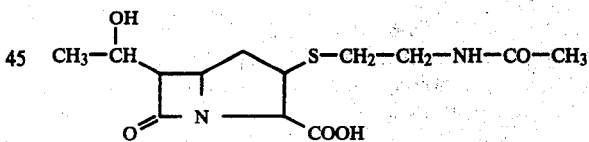

The present inventors previously discovered antibiotic OA-6129B of the following formula (Japanese Patent Application No. 144507/1980)

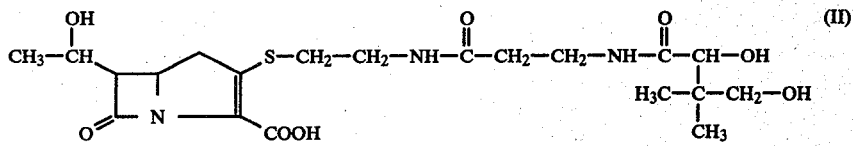

and antibiotics OA-6129A and antibiotic OA-6129C resulting from the replacement of the C-6

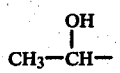

group of antibiotic OA-6129B by $CH_3CH_2-$ and

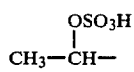

groups, respectively (Japanese Patent Applications Nos. 135829/1980 and 170864/1980).

The present inventors assumed a possibility that 2,3-dihydro compounds would also exist in the OA-6129 series of antibiotics as is the case with the above-mentioned structural relation of the No. 17927D substance to the KA-6643-A substance and No. 17927A substance. Based on this assumption, they searched for such 2,3-dihydro products in fermentation broths of OA6129 compounds-producing microorganisms, and finally discovered substances of the following formula

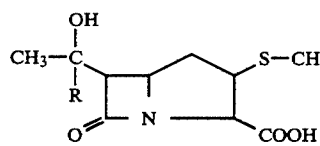
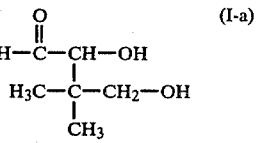

wherein R is as defined hereinabove.

The compounds of formula (I-a) provided by this invention have by far lower antimicrobial activity than the OA-6129 group of carbapenem antibiotics, but produce detectable halos on agar plate of *Comamonas terrigena*, B-996, a β-lactam-high sensitivity bioassay microorganism. The present inventors named the above compounds "antibiotic OA-6129D" [compound of formula (I-a) in which R is a hydrogen atom] and "antibiotic OA-6129E" [compound of formula (I-a) in which R is a methyl group].

It is highly probable that these antibiotics, OA-6129 D and E, will be converted to the OA-6129 group of carbapenem antibiotics having high antimicrobial potencies by dehydrogenation under suitable conditions known per se without eliminating the pantetheinyl group at the 3-position. For example, antibiotic OA-6129D can be converted to antibiotic OA-6129B by the action of intact cells, partially-treated mycelia and crude, partially purified or pure enzyme preparations of a compound OA-6129B-producing streptomycete. Or they can be converted to carbapenem antibiotics by dehydrogenation by a method known per se such as the process described in Japanese Laid-Open Patent Publication No. 76593/1979, in which, if necessary, after the hydroxyl groups in the C-3 side chain are protected, the removal of the pantotheinyl group by a chemical or biological method gives a compound of the following formula

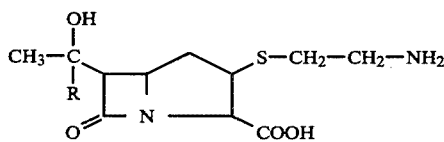

wherein R is as defined hereinabove, which is then dehydrogenated between C-2 and C-3 in the same manner as described above, with or without modification of the free amino group in the C-3 side chain.

Compounds of the invention other than those of formula (I-a), such as carboxylic esters of antibiotics OA-6129 D and E and their cyclic ketals and cyclic acetals have improved lipophilicity over antibiotics OA-6129 D and E themselves. Hence, they are easy to handle in lipophilic organic solvents, and are expected to find greater utility as intermediates for the derivation of carbapenem antibiotics by semi-synthetic methods.

Since the compounds of formula (I-b) provided by this invention have a carboxyl group at the 2-position, they can be in the form of salts or esters. Examples of the salts include salts with alkali metals such as sodium, potassium and lithium; salts with alkaline earth metals such as calcium and magnesium; salts with other metals such as aluminum; ammonium salts; salts with primary, secondary and tertiary amines such as monoethylamine, dimethylamine trimethylamine, monoethanolamine and diethanolamine; and salts with organic bases such as benzathine and procaine. Of these, pharmaceutically acceptable salts are preferred, and the alkali metal salts such as sodium and potassium salts are especially preferred.

Any ester residues known in the field of penicillin and cephalosporin chemistry can be used for the formation of the esters of the compounds of formula (I-a). Examples of such esters include benzyl, p-nitrobenzyl, p-methoxybenzyl, p-bromobenzyl, benzhydryl, trityl, phenacyl, phthalidyl, phthalimidomethyl, pivaloyloxymethyl, methoxymethyl, methylthiomethyl, and 2,2,2-trichloroethyl esters. In practice, unsubstituted or substituted benzyl esters are preferred. Thus, preferred ester residues for $R^1$ in formula (I) are unsubstituted or substituted benzyl groups of the following formula

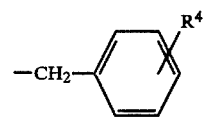

wherein $R^4$ represents a hydrogen atom, a halogen atom, a nitro group, or a lower alkoxy group preferably having 1 to 4 carbon atoms.

Alkylidene derivatives of the following formula

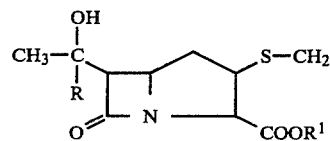
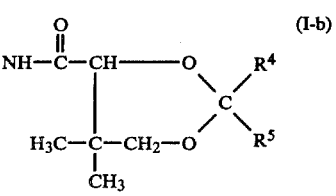

wherein R, $R^1$, $R^4$ and $R^5$ are as defined hereinabove, (i.e., cyclic ketal or acetal compounds) resulting from the simultaneous etherification of the α- and γ-position of the pantoyl group are other derivatives of antibiotics OA-6129 D and E.

If formula (I-b), the lower alkyl groups for $R^4$ and/or $R^5$ are linear or branched alkyl groups having not more than 6 carbon atoms, preferably 1 to 4 carbon atoms. Specific examples of the cyclic ketal or acetal group

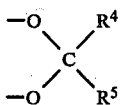

are as follows:

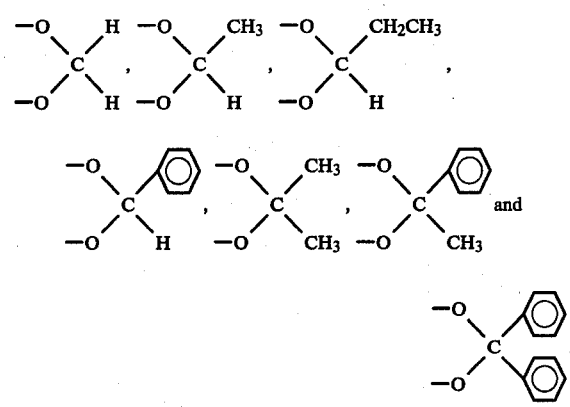

According to this invention, the compounds of formula (I), i.e. antibiotics OA-6129 D and E and/or the derivatives thereof, can be produced by a process which comprises cultivating a microorganism having the ability to produce antibiotics OA-6129 D and E in a nutrient medium, recovering antibiotics OA-6129 D and E from the culture broth, as required converting the resulting antibiotics to salts, and/or, if desired, esterifying the antibiotics or the salts thereof by a method known per se, and/or converting the antibiotics to cyclic acetals or ketals.

The microorganisms capable of producing antibiotics OA-6129 D and E having the chemical structure represented by formula (I-a) may belong to any genus, and can be selected from a wide range of microorganisms. Screening of microorganisms suitable for the object of this invention can be done by methods known per se. Anyone skilled in the art can easily obtain microorganisms capable of producing the antibiotics OA-6129 D and E.

Typical examples of the microorganisms include strains of the genus Streptomyces which have the ability to produce antibiotics OA-6129 D and E. One preferred example is Streptomyces species isolated from a soil sample collected near Sumiyoshi Shrine, Fukuoka-shi, Fukuoka-ken, Japan. This strain has the ability to produce both antibiotics OA-6129 D and E depending upon cultivating conditions, and is named OA-6129 strain by the present inventors.

The microbiological properties of the OA-6129 strain are shown below.

(1) MORPHOLOGY

On slide glass cultivation, straight to flexuous aerial mycelia without verticillate branches are seen to grow from well-branched substrate mycelia. The mature spore chain consists of at least 10 elliptical to cylindrical spores, and no sporangium is noted. The spores are about $(0.6 \sim 1.0) \times (0.7 \sim 2.5)$ microns in size and have smooth surfaces. No flagellated spore is observed.

(2) GROWTH IN VARIOUS CULTURE MEDIA

Cultivation is carried out at 28° to 30° C. unless specifically indicated otherwise. The colors are described mainly in accordance with the method described by H. D. Tresner and E. J. Backus (Journal of Applied Microbiology, Vol. 11, No. 4, pages 335 to 338 (1963)), and the symbols shown in parentheses [ ] are those given in Color Harmony Manual of Container Corporation of America (CHM code).

(1) Sucrose-nitrate agar

Yellowish gray [2dc] to grayish yellow pink [5dc] aerial mycelia occur on a moderate growth tinted with yellowish gray [2dc] to light grayish yellow brown [3ge]. No soluble pigment is formed.

(2) Glucose-asparagine agar

Light gray [d] aerial mycelia are observed on an abundant growth tinted with pale yellow [2db] to light olive brown [2ge], later turning grayish yellow pink [5dc]. No soluble pigment is observed.

(3) Glycerol-asparagine agar (ISP-5 medium)

Light gray [d] to light grayish redish brown [5fe] aerial mycelia occur on a good growth tinted with moderately yellowish pink [4gc] to light brown [4ie]. No soluble pigment is produced.

(4) Starch-inorganic salt agar (ISP-4 medium)

Light gray [d] aerial mycelia are formed on a good growth colored with pale yellow [2db] to gray [2fe]. No soluble pigment is noted.

(5) Tyrosine agar (ISP-7 medium)

Light gray [d] to light brownish gray [3fe] aerial mycelia on a grayish yellow [3ec] to light brown [4ie] growth are observed with slightly brownish pigmentation in the medium.

(6) Nutrient agar

Light grayish reddish brown [5fe] aerial mycelia occur on an abundant growth tinted with pale yellow [2db] or light yellow [2fb] to light olive brown [2ge]. No soluble pigment is noted.

(7) Yeast extract-malt extract agar (ISP-2 medium)

Grayish yellow pink [5dc], or at a somewhat later stage light gray [d], aerial mycelia on an abundant growth colored with moderately yellowish pink [4gc] to light brown [4ie] are observed without soluble pigment.

(8) Oatmeal agar (ISP-3 medium)

Light brownish gray [3fe] to light grayish reddish brown [5fe] aerial mycelia occur on a good growth tinted with grayish yellow [3ec] to light orange yellow [3ea]. The medium colors slightly brown around colonies.

(9) Calcium malate agar

Light gray [d] to light grayish reddish brown [5fe] aerial mycelia are noted on a moderate growth colored with dark to yellowish gray [2dc] without soluble pigment. The calcium salt dissolves around mature colonies.

(10) Glucose-peptone-gelatin (cultivated at 20° C.)

White [b] to grayish yellow pink [5cb] aerial mycelia occur on a good growth tinted with pale yellow [2db] to brown. When the cultivation period is prolonged (for more than about 3 weeks), a brown soluble pigment forms.

(3) PHYSIOLOGICAL PROPERTIES

(1) Growth temperature

The stain was cultivated on yeast extract-malt extract agar (ISP-2 medium) at temperatures of 10°, 20°, 25°, 30°, 34°, 37°, 40°, 45° and 50° C., respectively. It can scarcely grow at 37° C., and not at all at 40° C. or higher. Although it grows at the other temperatures, the optimal growth temperature appears to be in the range of 20° to 30° C.

(2) Liquefaction of gelatin

Positive.

(3) Hydrolysis of starch

Positive.

(4) Coagulation and peptonization of skimmed milk

Peptonized without coagulation.

(5) Formation of melanoid pigment

No melanoid pigment is formed in peptone-yeast extract-iron agar (ISP-6 medium) and tryptone-yeast extract broth (ISP-11 medium). In tyrosine agar, very slightly brown color is observed with a trace amount of melanin.

(4) UTILIZATION OF VARIOUS CARBON SOURCES (IN PRIDHAM AND GOTTLIEB AGAR)

| (1) | L-arabinose | + |
|---|---|---|
| (2) | D-xylose | + |
| (3) | D-glucose | + |
| (4) | D-fructose | + |
| (5) | sucrose | questionable |
| (6) | inositol | − |
| (7) | L-rhamnose | + |
| (8) | raffinose | − |
| (9) | D-mannitol | + |

+: utilized;
−: not utilized

From the above described microbiological properties, it is concluded that the OA-6129 strain is a streptomycete belonging to Section Rectiflexibiles. The surface of spores is smooth. The color of aerial mycelia is light gray [d] on most culture medium such as oatmeal agar, glycerol-asparagine agar and starch-inorganic salt-agar, indicating the gray series. But this strain sometimes produces grayish yellow pink [5dc] mycelia on sucrose-nitrate agar, yeast extract-malt extract agar and glucose-asparagine agar depending upon the phase of cultivation, suggesting the red series. The color of substrate mycelia is pale yellow to grayish yellow in an early stage of cultivation in all the treated culture media, later becoming yellowish brown to grayish yellow brown or brown. No formation of a melanoid pigment is observed in peptone-yeast extract-iron agar and tryptone-yeast extract broth. Other water-soluble pigments are not formed in most media, either. A slightly brown pigment is noted in tyrosine agar, glucose-peptone-gelatin and oatmeal agar.

The present inventors deposited this strain as Streptomyces sp. OA-6129 at Fermentation Research Institute, Agency of Industrial Science and Technology, Japan, 1-3, Higashi 1-chome, Yatabe-machi, Tsukuba-gun, Ibaraki-ken, Japan under the Budapest Treaty on the International Recognition of the Deposit of Microorganisms for the Purpose of Patent Procedure. Deposit Number FERM BP-11 has been assigned to this strain.

Antibiotics OA-6129 D and E of formula (I-a) of the invention can be produced by aerobical cultivation of a microorganism capable of producing antibiotics OA-6129 D and E, for example spores or mycelia of Streptomyces sp. OA-6129, in a nutrient medium.

Nutrient sources employed in this invention may be those commonly used for the cultivation of actinomycetes, such as carbohydrates, nitrogen sources and inorganic salts. They include, for example, carbohydrates such as glucose, glycerol, maltose, sucrose, molasses, dextrin and starch; oils and fats such as soybean oil, peanut oil and lard; nitrogen sources such as peptone, meat extract, soybean meal, cotton seed meal, dried yeast, corn steep liquor, yeast extract, skimmed milk, casein, sodium nitrate, ammonium nitrate and ammonium sulfate; and inorganic salts such as dipotassium phosphate, sodium chloride, calcium carbonate and magnesium sulfate. If required, traces of metals such as cobalt and manganese may be added to the culture medium. Other nutrient sources may also be used, as far as they can support the growth of microorganisms having the ability to produce antibiotics OA-6129 D and E, and lead to the substantial production of antibiotics OA-6129 D and E. Accordingly all nutritional materials for known actinomycetes can be used. An antifoamer such as silicones and vegetable oils may be added to prevent foaming during autoclaving and cultivation.

The mixing proportions of the aforesaid nutrient sources are not particularly restricted, and can be varied over a wide range. The optimum compositions and mixing proportions of nutrient sources for the producing microorganisms can be easily determined by anyone skilled in the art through a simple small-scale experiment.

The nutrient medium may be sterilized prior to cultivation. Advantageously, the pH of the culture medium is adjusted to a range of 4 to 9, preferably a range of 6 to 8, before or after sterilization.

Cultivation of the producing microorganisms in such culture media can, in principle, be carried out in accordance with methods usually employed for the production of antibiotics by actinomycetes. Usually, the cultivation is suitably carried out under aerobic conditions, for example, with stirring and/or forced aeration. Although the method of cultivation may be stationary, shaken or submerged with aeration and agitation, the submerged cultivation is advantageous.

The cultivation temperature may be in any range of temperature, as far as it does not inhibit substantial growth of the producing microorganism, resulting in the formation of antibiotics OA-6129 D and E. The suitable cultivation temperature varies depending upon the microorganism to be used, and is generally 20° to 40° C., preferably 25° to 35° C.

For better antibiotic production, the pH of the culture broth may be adjusted to 4 to 9, especially 6 to 8, during cultivation.

In the case of large-scale fermentation intended for mass production, it is advantageous to perform seed cultivation, main cultivation in production medium under submerged conditions.

The cultivation can usually be continued until substantial amounts of antibiotic OA-6129 D and E are accumulated in the broth. The cultivation period is usually 30 to 90 hours, although it may vary depending upon the composition of the culture medium, the cultivation temperature, the microorganism used, etc.

Needless to say, anyone skilled in the art would easily be able to determine optimal cultivation conditions depending upon the properties of the particular microorganism, by performing simple experiments.

The amounts of the compounds of formula (I-a) accumulated in the broth can be determined by bioassy or bioautography using $\beta$-lactam-high sensitivity bioassay organisms such as *Comamonas terrigena* B-996. By such analysis, the optimal timing of harvest can be easily determined.

The compounds of formula (I-a) accumulated in the culture broth are water-soluble and thus are largely present extra-cellularly. Advantageously, the microbial cells after cultivation are removed by a known separating method such as filtration, centrifugation and extraction so that the compounds are recovered from the resulting filtrate, supernatant, extract, and the like.

Although the compounds of formula (I-a) can be isolated by various methods known per se, it is advantageous to employ methods frequently utilized for the isolation of carboxylic antibiotics. Examples of such methods are extraction at a low pH with a solvent such as ethyl acetate and n-butanol followed by transfer into an aqueous layer at a high pH; adsorption on activated carbon, Amberlite XAD (a product of Rohm & Haas Co.), Diaion HP-20 (a product of Mitsubishi Chemical Industries Ltd.), etc. followed by elution with methanol/water, acetone/water, etc.; adsorption on an ion exchange resin such as Dowex 1×2 (a product of Dow Chemical Co.) QAE-Sephadex A-25 (a product of Pharmacia Fine Chemicals AB), DEAE-Cellulose Whatman DE-32 (a product of Whatman Ltd.) and DEAE-Sephadex A-25 (a product of Pharmacia Fine Chemicals AB) followed by elution; gel filtration on Sephadex G-10 (a product of Pharmacia Fine Chemicals AB), Biogel P-2 (a product of Bio-Rad Laboratories), etc.; column chromatography using cellulose, e.g. Avicel (a product of American Viscose Corporation); forced precipitation by addition of a solvent such as acetone; and lyophilization. These methods can be used either singly or in combination. If required, they may be performed repeatedly. In this manner, the compounds of formula (I-a) are obtained.

In the compounds of formula (I-a) obtained by fermentation the hydrogen atoms at C-5 and C-6 may have a trans- or cis-configuration, and the formula (I-a) encompasses a 5,6-trans form, a 5,6-cis form and a mixture of these. Furthermore, since C-2, C-3, C-8 and the carbon atom having the secondary hydroxyl group in the C-3 pantetheinyl side chain are asymmetric, the compounds of formula (I-a) may have possible combinations of R and S at the said carbon atoms or be a racemic mixture thereof.

Generally, the compounds of formula (I-a) are more stable in the form of salt or ester than in free form. Hence, when they are to be used as an intermediate for chemical derivation or subjected to purification steps described above, it is convenient and advantageous to treat them in the form of a salt or ester.

The compounds of formula (I-a) can be converted to their salts or esters by methods known per se. For example, salts of the compounds of formula (I-a) can be produced by treating the free compounds of formula (I-a) with inorganic or organic bases. Examples of inorganic or organic bases which can be used in salification include alkali metal hydroxides such as sodium hydroxide, potassium hydroxide and lithium hydroxide; alkaline earth metal hydroxides such as calcium hydroxide and magnesium hydroxide; and primary, secondary and tertiary organic amines such as monoethylamine, dimethylamine, trimethylamine, monoethanolamine, diethanolamine, benzathine and procaine.

The compounds of formula (I-a) can be esterified by the same methods as used for esterification of antibiotic PS-5, etc., for example by the method described in Japanese Laid-Open Patent Publication No. 84589/1979. More particularly, the antibiotics can be easily esterified by stirring salts of the compounds of formula (I-a) with a compound of the formula $R^{11}X$ in which X is a halogen atom and $R^{11}$ is an ester residue, in the presence of an organic base, an alkali metal or an alkaline earth metal, in an inert solvent such as dimethylformamide, tetrahydrofuran, dioxane, hexamethylphosphoric triamide, acetonitrile or acetone, at a temperature of about $-50°$ C. to 50° C., preferably at a temperature of about $-10°$ C. to 30° C. for a period of several minutes to several hours.

The esters of the compounds of formula (I-a) obtained in the above-described manner can be converted to cyclic ketal or acetal derivatives by simultaneously etherifying the $\alpha$ and $\gamma$ hydroxyl groups of the C-3 pantetheinyl side chain by known methods.

For example, the compounds of formula (I-a) can be converted to their cyclic ketal or acetal derivatives by treating their esters with ketones or aldehydes. In general, the reaction is preferably carried out by using the reagent itself as a solvent. Examples of useful reagents are acetone, 2,2-dimethoxypropane, formaldehyde, 2,2-dimethoxyethane, acetaldehyde, benzaldehyde, propionaldehyde, acetophenone and diphenylketone. These reagents may be used singly or as required in a combination of two or more.

The amount of the reagent is not critical.

As required, in view of the solubility of the compound of formula (I-a) in the reagent, an inert solvent such as dimethylformamide, chloroform, tetrahydrofuran tetrahydrafran and ethylenchloride may be used in combination.

The reaction temperature is not critical, and can be varied widely depending upon the type of the solvent as far as the ester of the compound of formula (I-a) is substantially stable. It is generally not more than 60° C., preferably $-40°$ to 40° C., and more preferably 0° C. to room temperature.

If necessary, a suitable amount of a reaction promoter may be added in the above reaction. Examples of the promoter are anhydrous p-toluenesulfonic acid, boron trifluoride etherate, and zinc chloride.

Under the above reaction conditions, the reaction can be terminated in about 30 minutes to about 12 hours, usually in 2 to 5 hours.

The resulting cyclic ketal or acetal derivatives of the above esters can be isolated from the reaction mixtures by known methods for isolation and purification. For example, the reaction mixture is treated with an amine for inactivation of the excess of the reaction promoter, and the treated mixture is poured into a substantially water-immiscible nonpolar organic solvent such as ethyl acetate, benzene and chloroform. The mixture is then washed with an aqueous solution so that water-soluble impurities including by-products may be removed. Desirably, the aqueous solution is a neutral buffer. Then the organic solvent layer is separated and concentrated to dryness. The desired cyclic ketal or acetal derivative can be isolated and purified by a suitable combination of known methods, for example, column chromatographic methods on silica gel, Bio-Beads (a product of Bio-Rad Laboratories), Sephadex LH-20 (a product of Pharmacia Fine Chemicals AB) and other supporting materials. If required, the purification procedure is repeated.

The compounds of formula (I-a) and their salts provided by this invention are useful as synthetic intermediates for synthesis of various carbapenem antibiotics (see Referential Examples 1 to 4 given hereinbelow). They are also expected to be useful as dehydrodipeptitase inhibitors or prodrugs for carbapenem antibiotics.

The following examples illustrate the present invention in greater detail.

EXAMPLE 1

Fermentative production of sodium 6-(1-hydroxyethyl)-3-pantetheinyl-7-oxo-1-azabicyclo[3.2.0]heptane-2-carboxylate (antibiotic OA-6129D) of the following formula

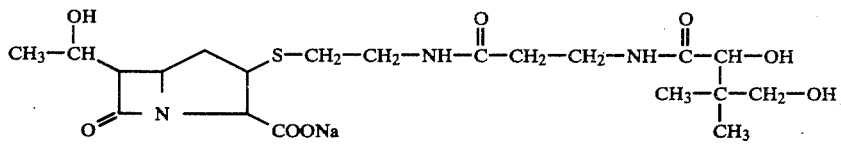

(A) One hundred milliliters of a seed culture medium (S-1) having the composition shown below as put into a 500 ml Erlenmeyer flask, and sterilized at 120° C. for 15 minutes. A loopful of mature spores of Streptomyces sp. OA-6129 (FERM BP-11) was inoculated in the seed culture medium, and cultivated at 28° C. for 48 hours with shaking on a rotary shaker (200 rpm, throw 7 cm). One liter of the seed culture was transferred to a 2000-liter fermentor containing 1000 liters of a production medium (GM-1) having the composition shown below, and aerobically cultivated for 90 hours at 28° C. at an aeration rate of 500 liters/min. with stirring at 150 rpm. As an antifoamer, 0.07% of Silicone KM-75 (a product of Shin-etsu Chemical Co., Ltd.) was added. The culture broth was periodically sampled and centrifuged. The resulting supernatant was assayed for antimicrobial activity. The results were as shown in the following table.

| Cultivation time (hours) | Antimicrobial titer (μg/ml) |
|---|---|
| 48 | 0.5 |
| 72 | 4.2 |
| 90 | 12.5 |

Composition of the seed culture medium (S-1)

| Soybean meal | 1.5% (W//V) |
|---|---|
| Yeast extract | 0.5% (W//V) |
| Potato starch | 2.0% (W//V) |
| CaCO3 | 0.2% (W//V) |
| ph (before sterilization) | 7.0 |

Composition of the production medium (GM-1)

| Glycerol | 8.0% (W/V) |
|---|---|
| Fish meal | 1.0% (W/V) |
| Soybean meal | 3.0% (W/V) |
| CaCo3 | 0.3% (W/V) |
| K2HPO4 | 0.2% (W/V) |
| MgSO4 | 0.2% (W/V) |
| ph (adjusted to 7.2 with NaOH) | |

Vitamin $B_{12}$ in 0.01 M phosphate buffer, pH 5.5, was separately autoclaved for 5 minutes at 1 kg/cm$^2$.G, and added in an amount of 0.0005% (W/V).

(B) Topco Perlite No. 34 (a product of Toko Perlite Kabushiki Kaisha) was added in an amount of 5% (W/V) to 950 liters of the 90 hour-old fermentation broth obtained in (A). The suspension was centrifuged with a basket-type centrifuge to give 900 liters of the broth filtrate.

The filtrate was adsorbed on a column (30×300 cm) of Diaion HP-20. The column was washed with 10 liters of distilled water and then eluted with 30% (V/V) aqueous acetone. The eluate was fractionated into 1-liter volumes. Fractions Nos. 6 to 18 (13 liters in total) were collected and adsorbed on a column (10×100 cm) of Diaion PA306S (a product of Mitsubishi Chemical Co., Ltd.). The column was washed with 10 liters of distilled water and eluted with 0.01 M phosphate buffer, pH 8.4, containing 3.0% of sodium chloride. The eluate was fractionated into 1-liter volumes. Fractions Nos. 7 to 21 (15 liters in total), were collected and adsorbed on a column (10×100 cm) of Diaion HP-20 and the column was eluted with 40 liters in total of aqueous acetone by using a linear concentration gradient of acetone from 0 to 30%. The eluate was divided into 200 ml fractions, and the fractions were bioassayed. Active fractions Nos. 52 to 59 were obtained in a total amount of 1600 ml. These active fractions were divided into four 400 ml portions. Each portion was charged onto a column (8×100 cm) of Bio-Gel P-2 which had been equilibrated with 0.01 M phosphate buffer, pH 8.4, and the column was developed with the aforesaid buffer. By bioassay, 7.4 ml of active fractions were collected. These active fractions were adsorbed on a column (8×100 cm) of QAE Sephadex A-25. The active eluate was carefully adjusted to pH 8.4 wsth 10% NaOH, and adsorbed on a column (4×100 cm) of Diaion HP-20. The column was eluted with 6.0 liters in total of aqueous acetone by using a linear concentration gradient of acetone from 0 to 30%. The eluate was fractionated into 15 ml fractions. Fractions Nos. 45 to 64 containing antibiotics OA-6128 B and D were collected in a total amount of 300 ml, and lyophilized to give 2.2 g of a pale yellow powder.

The resulting powder (2 g) of antibiotics OA-6129 B and D was dissolved in a small amount of water and charged onto a column (1.5×80 cm) of Sephadex G-10 which had been equilibrated with 0.01 M phosphate buffer, pH 8.4. The column was developed with the aforesaid buffer, and 30 ml of active fractions were collected by bioassay. The active fractions were adsorbed onto a column (2.5×40 cm) of QAE Sephadex A-25 which had previously been equilibrated with the aforesaid buffer. The column was washed with 180 ml of the aforesaid buffer, and eluted with a linear concentration gradient of sodium chloride from 0 to 2.0% in the same buffer. The eluate was fractionated into 15 ml fractions, and active fractions Nos. 20 to 36 were collected by bioassay, (total volume 250 ml).

The active fractions were lyophilized and then dissolved in a small amount of water. The solution was adsorbed to a column (1.5×110 cm) of Diaion HP-20AG. The column was washed with about 200 ml of distilled water, and eluted with 1.2 liters in total of aqueous acetone by using a linear concentration gradient of acetone from 0 to 6%. The eluate was fractionated into 10 ml fractions, and active fractions were obtained by bioassay. Fractions Nos. 25 to 69 (total volume 450 ml) contained antibiotics OA-6129B and D, and fractions Nos. 70 to 79 (total volume 100 ml) antibiotic OA-6129A.

By lyophilization, 410 mg of a mixture of sodium salts of antibiotics OA-6129B and D and 54 mg of the sodium salt of antibiotic OA-6129A were obtained.

EXAMPLE 2

Isolation of p-nitrobenzyl ester of 6-(1-hydroxyethyl)-3-pantetheinyl-7-oxo-1-azabicyclo[3.2.0]heptane-2-carboxylic acid (antibiotic OA-6129D)

Six hundred milligrams of a pale yellow powder composed of sodium salts of antibiotics OA-6129B and D as obtained in Example 1 was dissolved in 30 ml of dimethylformamide, and then mixed with 2.0 ml of triethylamine under cooling with ice. With stirring, a solution of 2.7 g of p-nitrobenzyl bromide in a small amount of dimethylformamide was added. The reaction was carried out at the same temperature for 5 minutes, and then at room temperature for 3 hours. The reaction mixture was poured into 100 ml of methylene chloride, mixed, and washed with two 30 ml portions of 0.1 M phosphate buffer, pH 6.8, saturated with sodium chloride. The aqueous layer (60 ml) was again extracted with two 100 ml portion of methylene chloride. The organic extracts were combined and dehydrated over anhydrous sodium sulfate. After the solvent was evaporated off under reduced pressure, the residue was dissolved in a small amount of methylene chloride and adsorbed onto a column of 60 g of silica gel using benzene/acetone (1/1). The column was developed successively with mixture of benzene and acetone (1:1 and 1:3) and acetone. Fractions eluted with the 1:3 benzene-acetone mixture and acetone were collected and concentrated to give 240 mg of p-nitrobenzyl ester of antibiotic OA-6129D which showed a UV-absorbing spot at Rf 0.52 on a silica gel thin-layer chromatographic plate developed in a 1:4 benzene/acetone mixture, and showed antimicrobial activity on an assay plate of *Comamonas terrigena* B-996 containing horse serum. Further elution of the silica gel column with acetone yielded fractions containing p-nitrobenzyl ester of OA-6129B. Concentrating the fractions gave 250 ml of p-nitrobenzyl ester of antibiotic OA-6129B which showed Rf 0.23 on a silica gel thin-layer chromatographic plate developed with a 1:4 benzene/acetone mixture.

The p-nitrobenzyl ester of antibiotic OA-6129D obtained in the above manner had the following properties.

Specific rotation: $[\alpha]_D^{24}$ 11.7° (c=1.0, CH$_2$Cl$_2$).

IR Spectrum: $\nu_{max}^{CHCl_3}$ cm$^{-1}$: 1750 ($\beta$-lactam, ester), 1660 (amide).

UV Spectrum: $\lambda_{max}^{CH_2Cl}$ nm($\epsilon$): 268(5500).

NMR Spectrum (CDCl$_3$): δ:

0.90 (3H, s,

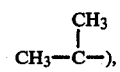

), 0.98 (3H, s,

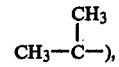

), 1.34 (2H, d, J=6.5 Hz, C$\underline{H_3}$—CH), 1.75–2.20 (3H, m, C-4H$_2$, OH), 2.30–2.80 (5H, m, S—C$\underline{H_2}$—CH$_2$—NH, NH—CH$_2$—C$\underline{H_2}$—CO, OH), 3.15–4.50 (12H, m, C-3H, C-5H, C-6H, C-8H, NH—C$\underline{H_2}$—CH$_2$—CO, S—CH$_2$—C$\underline{H_2}$—NH,

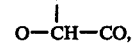

O—C$\underline{H_2}$—C, OH)

4.77 (1H, d, J=7.0 Hz, C-2H), 5.23 (2H, s, C$\underline{H_2}$—Ar), 6.70 (1H, br, NH), 7.30–7.60 (3H, m, Ar—$\underline{H}$, NH), 8.17 (2H, d, J=8.0 Hz, AR—$\underline{H}$).

Mass Spectrum (FD): m/z 611 (M+1).

EXAMPLE 3

Production of p-nitrobenzyl 6-(1-hydroxyethyl)-3-isopropylidenepantetheinyl-7-oxo-1-azabicyclo[3.2.0]heptane-2-carboxylate

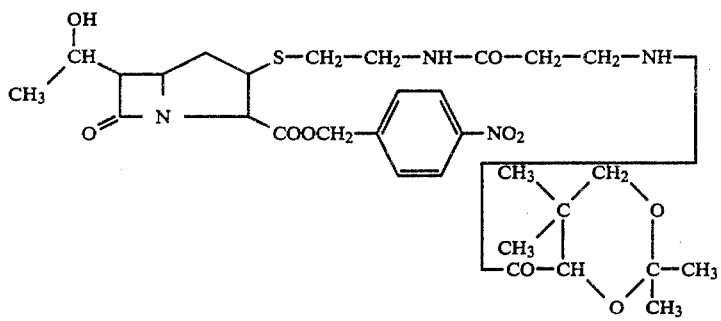

Fifty-two mg of p-nitrobenzyl ester of antibiotic OA-6129D was dissolved in a mixed solvent consisting of 4.0 ml of acetone, 0.5 ml of 2,2-dimethoxypropane and 200 mg of anhydrous sodium sulfate, and with stirring at room temperature, 1.5 mg of p-toluenesulfonic acid was added. The reaction was carried out for 30 minutes, and 20 μl of triethylamine was added to the reaction mixture. The mixture was kept stirred for a further 5 minutes. After the solvent was evaporated under reduced pressure, 30 ml of methylene chloride was added to the residue. The organic solution was washed successively with 20 ml of 0.1 M phosphate buffer, pH 8.4, and 20 ml of 0.1 M phosphate buffer, pH 6.8. The organic layer was dehydrated with anhydrous sodium sulfate and concentrated to dryness under reduced pressure. The residue was dissolved in a small volume of methylene chloride and adsorbed onto a column of 5 g of silica gel by using a 10:1 mixture of benzene and acetone. The column was developed successively with mixtures of benzene and acetone by increasing stepwise the concentration of acetone as follows: 10:1, 5:1, 3:1, 1:1, and 1:3. The active fractions eluted with 1:1 and 1:3 mixtures of benzene and acetone were collected and concentrated to dryness under reduced pressure to give 31 mg of the captioned compound which showed Rf 0.35 on a silica gel thin-layer chromatographic plate developed with a 1:1 mixture of benzene and acetone.

This product had the following properties.

Specific rotation: $[\alpha]_D^{24}$ 20.3° (c=1.0, CH$_2$Cl$_2$).

IR Spectrum: $\nu_{max}^{CHCl_3}$ cm$^{-1}$: 1750 (β-lactam, ester), 1660 (amide).

UV Spectrum: $\lambda_{max}^{CH_2Cl_2}$ nm(ε): 268 (7500).

NMR Spectrum (CDCl$_3$): δ:

0.96 (3H, s,

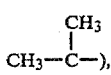

1.02 (3H, s,

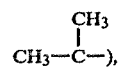

1.36 (3H, d, J=7.0 Hz, C$\underline{H}_3$—CH),
1.42 (3H, s,

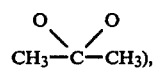

1.46 (3H, s,

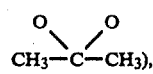

1.60-2.20 (2H, m, C-4H$_2$),
2.42 (2H, t, J=6.5 Hz, NN—CH$_2$—C$\underline{H}_2$—CO),
2.50-2.70 (2H, m, S—C$\underline{H}_2$—CH$_2$—N$\overline{H}$),
2.85 (1H, d, J=5.0 Hz, O$\overline{H}$),
3.15-3.85 (8H, m, S—CH$_2$—C$\underline{H}_2$—NH, NH—C$\underline{H}_2$—CH$_2$—CO, C-3H, C-6H, O—CH$_2$—C),
4.04 (1H, s

3.90-4.20 (2H, m, C-5H, C-8H),
4.77 (1H, d, J=7.5Hz, C-2H),
5.27 (2H, s, C$\underline{H}_2$—Ar),
6.42 (1H, br, N$\overline{H}$),
6.97 (1H, br, NH),
7.50 (2H, d, J=8.5 Hz, Ar—$\underline{H}$),
8.18 (2H, d, J=8.5 Hz, Ar—$\underline{H}$).
Mass Spectrum (FD): m/z: 651 (M+1).

EXAMPLE 4

Fermentative production of sodium 6-(1-hydroxy-1-methyl)ethyl-3-pantetheinyl-7-oxo-1-azabicyclo[3.2.0]heptane-2-carboxylate (antibiotic OA-6129E)

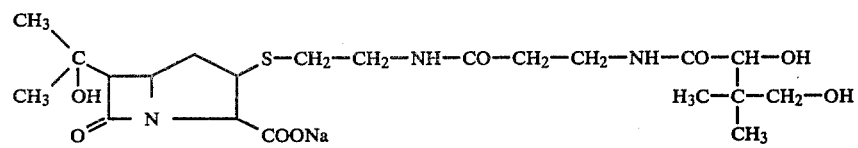

To 950 liters of the 90-hour old fermentation broth as obtained in section (A) of Example 1 was added 5%(W/V) to Topco Perlite No. 34. The suspension was filtered through a filter press to give 900 liters of the fermentation filtrate.

The filtrate was adsorbed onto a column (30×300 cm) of Diaion HP-20. The column was washed with 10 liters of distilled water and eluted with 30% (V/V) aqueous acetone. The eluate was fractionated into 1-liter volumes. Fractions Nos. 11 to 24 (total amount 14 liters) were collected, and adsorbed onto a column (10×100 cm) of Diaion Pa306S (a product of Mitsubishi Chemical Co., Ltd.). The column was washed with 10 liters of distilled water and then eluted with 0.01 M phosphate buffer, pH 8.4, containing 3.0% of sodium chloride. The eluate was fractionated into 1-liter volumes, and fractions Nos. 6 to 20 were collected to give 15 liters of the active solution.

The active solution was adsorbed onto a column (10×100 cm) of Diaion HP-20 and eluted with 40 liters in total of aqueous acetone by using a linear concentration gradient of acetone from 0 to 30%. The eluate was fractionated into 200 ml amounts, and antimicrobially active fractions Nos. 55 to 62 (1600 ml in total) were obtained by bioassay.

The solution was divided into four 400 ml portions. Each portion was charged onto a column (8×100 cm) of Bio-Gel P-2 which had been equilibrated with 0.01 M phosphate buffer, pH 8.4, and the column was developed with the same buffer. By bioassay, 7.0 liters in total of antimicrobially active fractions were collected. These active fractions were adsorbed onto a column (8×100 cm) of QAE Sephadex A-25 which had been equilibrated with the same buffer. The eluate was carefully adjusted to pH 8.4 with 10% NaOH, and then adsorbed onto a column (4×100 cm) of Diaion HP-20 which had been equilibrated with 0.01 M phosphate buffer, pH 8.4. The column was eluted with 6.0 liters in total of aqueous acetone by using a linear concentration gradient of acetone from 0 to 30%. The eluate was fractionated into 15 ml volumes, and 300 ml of fractions Nos. 48 to 67 containing antibiotics OA-6129$B_2$ [the 5,6-cis isomer of the compound of formula (II)], D and E. Lyophilization of these fractions gave 12 g of a brown powder.

The resulting powder (12 g) containing OA-6129 $B_2$, D and E was dissolved in a small amount of water, and charged onto a column (1.5×80 cm) of Sephadex G-10 which had been equilibrated with 0.01 M phosphate buffer, pH 8.4. The column was developed with the same buffer, and 30 ml of antimicrobially active fractions were collected by bioassay. The active fractions were adsorbed onto a column (2.5×40 cm) of QAE Sephadex A-25 which had been equilibrated with the same buffer. The column was washed with 180 ml of the same buffer, and then eluted with a linear concentration gradient of sodium chloride from 0 to 2.0% in the same buffer. The eluate was fractionated into 15 ml volumes, and antimicrobially active fractions Nos. 22 to 38 were collected by bioassay to give a total amount of about 250 ml.

These active fractions were lyophilized, and dissolved in a small amount of water. The solution was adsorbed onto a column (1.5×110 cm) of Diaion HP-20 AG (a product of Mitsubishi Chemical Co., Ltd.). The column was washed with about 200 ml of distilled water, and eluted with 1.2 liters in total of aqueous acetone by using a linear concentration gradient of acetone from 0 to 6%. The eluate was fractionated in 10 ml portions, and antimicrobially active fractions were obtained by bioassay. Among the active fractions, fractions Nos. 27 to 71 (total amount 450 ml) contained antibiotics OA-6129 $B_2$, D and E. Lyophilization gave 1.3 g of a crude powder containing a mixture of sodium salts of antibiotics OA-6129 $B_2$, D and E.

EXAMPLE 5

Isolation of p-nitrobenzyl ester of 6-(1-hydroxy-1-methylethyl-3-pantetheinyl-7-oxo-1-azabicyclo[3.2.0]heptane-2-carboxylic acid (antibiotic OA-6129E)

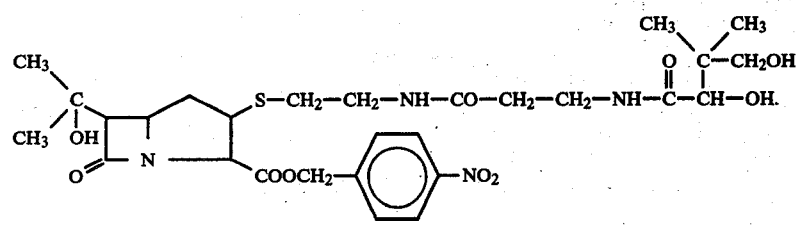

A pale yellow crude powder (1.3 g) composed of sodium salts of antibiotics OA-6129 $B_2$, D and E obtained in Example 4 was dissolved in 50 ml dimethylformamide. While the solution was cooled with ice, 2.5 ml of triethylamine was added, and with stirring, 2.7 g of p-nitrobenzyl bromide dissolved in a small amount of dimethylformamide was added. The reaction was carried out at the same temperature for 5 minutes, and then at room temperature for 3 hours. The reaction mixture was poured into 300 ml of methylene chloride, and washed twice with 50 ml each of 0.1 M phosphate buffer, pH 6.8. The aqueous layers were combined and again extracted with two 100 ml portions of methylene chloride. The organic layer and washings were combined, dehydrated with anhydrous sodium sulfate, and evaporated to dryness under reduced pressure. The residue was dissolved in a small amount of methylene chloride, and adsorbed onto a column of 50 g of silica gel by using a 1:1 mixture of benzene and acetone. The column was developed successively with 1:1 and 1:3 mixtures of benzene and acetone, and with acetone. Active fractions eluted with the 1:3 benzene-acetone mixture were collected and concentrated to dryness to give 320 mg of p-nitrobenzyl ester of antibiotic OA-6129E which showed a UV-absorbing spot at Rf 0.55 on a silica gel thin-layer chromatographic plate developed with a 1:3 mixture of benzene and acetone.

EXAMPLE 6

Production of p-nitrobenzyl 6-(1-hydroxy-1-methyl)ethyl-3-isopropylidenepantetheinyl-7-oxo-1-azabicyclo[3.2.0]heptane-2-carboxylate

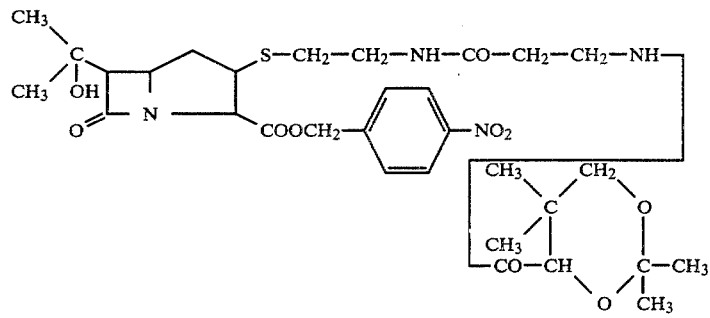

p-Nitrobenzyl ester of antibiotic OA-6129E (320 mg) was dissolved in a mixed solvent consisting of 10 ml of acetone, 1.0 ml of 2,2-dimethoxypropane and 200 mg of anhydrous sodium sulfate. With stirring at room temperature, 7.0 mg of p-toluenesulfonic acid was added, and the reaction was carried out for 30 minutes. After 0.1 ml of triethylamine was added, the mixture was stirred for a further 5 minutes and then concentrated to dryness under reduced pressure. Methylene chloride (100 ml) was added to the residue, and the solution was washed successively with 20 ml of 0.1 M phosphate buffer, pH 8.4 and 20 ml of 0.1 M phosphate buffer, pH 6.8. The organic layer was dehydrated with anhydrous sodium sulfate, and subjected to evaporation under reduced pressure. The residue was dissolved in a small amount of methylene chloride, and adsorbed onto a column of 5 g of silica gel by using a 10:1 mixture of benzene and acetone. The column was developed successively with benzene-acetone mixtures by increasing stepwise the acetone concentration as follows: 10:1, 5:1, 3:1, 1:1 and 1:2. Active fractions eluted with the 1:1 and 1:2 mixtures of benzene and acetone were collected and concentrated under reduced pressure to give 210 mg of the captioned compound which showed Rf 0.54 on a silica gel thin-layer chromatographic plate developed with a 1:1 mixture of benzene and acetone.

The resulting compound had the following properties:

Specific rotation: $[\alpha]_D^{24}$ 12.6° (c=1.0, CHCl$_3$).

UV Spectrum: $\lambda_{max}^{CHCl_3}$ nm($\epsilon$): 268 (21500).

IR Spectrum $\nu_{max}^{CHCl_3}$ cm$^{-1}$: 1750 ($\beta$-lactam, ester), 1662 (amide).

NMR Spectrum (CDCl$_3$ internal standard TMS): δ:
0.97 (3H, s,

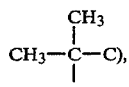

1.03 (3H, s,

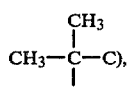

1.28 (3H, s,

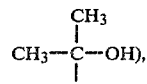

1.41 (3H, s,

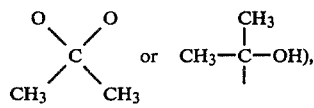

1.45 (3H, s,

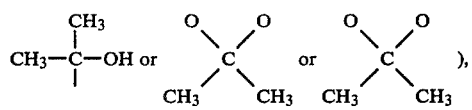

1.46 (3H, s,

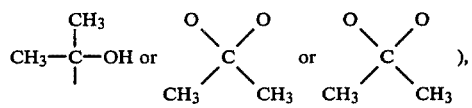

1.65–2.15 (2H, m, C-4H$_2$),
2.25–2.70 (5H, m, NH—CH$_2$—C$\underline{H_2}$—CO, OH, S—CH$_2$—C$\underline{H_2}$—NH),
2.80–3.85 (8H, m, C-3H, C-6H, S—C$\underline{H_2}$—CH$_2$—NH, NH—C$\underline{H_2}$—CH$_2$—CO,

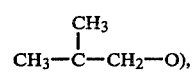

3.90–4.30 (1H, m, C-5H),
4.03 (1H, s,

4.73 (1H, d, J=7.5 Hz, C-2H),
5.23 (2H, s, C$\underline{H_2}$—Ar),
6.30 (1H, br, N$\underline{H}$),
6.93 (1H, br, NH),
7.50 (2H, d, J=8.5 Hz, Ar—$\underline{H}$),
8.17 (2H, d, J=8.5 Hz, Ar—$\underline{H}$).
Mass spectrum: M/Z: 664 (M$^+$).

From the above described physical data, it was concluded that the captioned compound had the structural formula given under the caption.

REFERENTIAL EXAMPLE 1

Production of p-nitrobenzyl 6-(1-acetoxyethyl)-3-isopropylidenepantetheinyl-7-oxo-1-azabicyclo[3.2.0]heptane-2-carboxylate

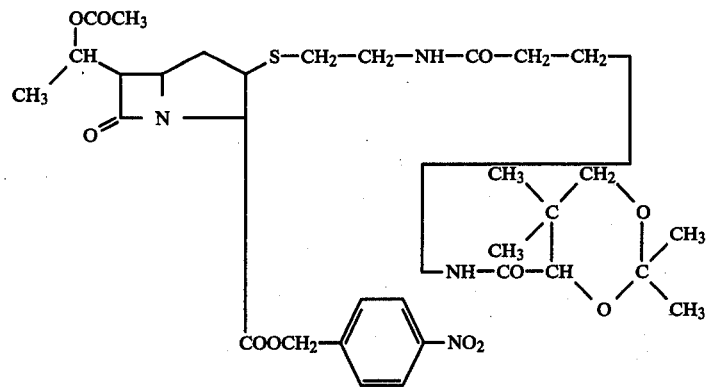

Twenty-five milligrams of the compound produced in Example 3 was dissolved in 1 ml of pyridine. Under cooling with ice, 0.32 ml of acetic anhydride was added with stirring. The reaction was carried out at the same temperature for 5 minutes, and then at room temperature for 3 hours. Ice water was added to the reaction mixture. The mixture was stirred for 10 minutes, and poured into 50 ml of methylene chloride. The solution was washed successively with 20 ml of 0.1 M phosphate buffer, pH 6.8, 40 ml of 0.1 M phosphate buffer, pH 8.4, and 20 ml of 0.1 M phosphate buffer, pH 6.8. The organic layer was dehydrated with anhydrous sodium sulfate and evaporated to dryness under reduced pressure. The residue was dissolved in a small amount of methylene chloride, and adsorbed onto a column of 5 g of silica gel with benzene. The column was developed successively with benzene-acetone mixtures by raising stepwise the concentration of acetone as follows: 10:0, 10:1, 5:1, 3:1, 2:1, 1:1, and 1:5. Active fractions eluted with the 1:1 mixture of benzene and acetone were collected and concentrated to dryness to give 18 mg of the captioned compound which showed a UV absorbing spot at Rf 0.61 on a silica gel thin-layer chromatographic plate developed with a 1:1 mixture of benzene and acetone. The resulting compound had the following properties:

Specific rotation: $[\alpha]_D^{24}$ 12.5° (c=1.0, CH$_2$Cl$_2$).

IR Spectrum: $\nu_{max}^{CHCl_3}$ cm$^{-1}$: 1768 ($\beta$-lactam), 1740 (ester), 1665 (amide).

UV Spectrum: $\lambda_{max}^{CH2Cl2}$ nm($\epsilon$): 268 (10100).

NMR Spectrum (CDCl$_3$) δ:

0.97 (3H, s,

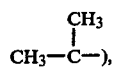

1.02 (3H, s

CH$_3$—C(CH$_3$)—), 1.30 (3H, d, J=6.5 Hz, CH$_3$—CH),
1.40 (3H, s, $$CH_3-\underset{O}{\overset{O}{\diagup\diagdown}}-CH_3),$$

1.44 (3H, s, $$CH_3-\underset{O}{\overset{O}{\diagup\diagdown}}-CH_3),$$

2.05 (3H, s, CH$_3$CO),
1.80–2.28 (2H, m, C-4H$_2$),
2.40 (2H, t, J=6.5 Hz, NH—CH$_2$—CH$_2$—CO),
2.55–2.90 (2H, m, S—CH$_2$—CH$_2$—NH),
3.10–3.80 (8H, m, S—CH$_2$—CH$_2$—NH, NH—CH$_2$—CH$_2$—CO, C-3H, C-6H, O—CH$_2$—C),
4.01 (1H, s,

O—CH—CO), 4.00–4.20 (1H, m, C-5H),
4.72 (1H, d, J=7.0 Hz, C-2H),
4.98–5.30 (1H, m, C-8H),
5.23 (2H, s CH$_2$—Ar),
6.34 (1H, br, NH),
6.93 (1H, br, NH),
7.48 (2H, d, J=9.0 Hz, Ar—H),
8.17 (2H, d, J=9.0 Hz, Ar—H).

Mass Spectrum: FD m/z: 693 (M+1), IB m/z: 692 (M).

REFERENTIAL EXAMPLE 2

Production of p-nitrobenzyl 6-(1-acetoxyethyl)-3-chloro-3-isopropylidenepantetheinyl-7-oxo-1-azabicyclo[3.2.0]heptane-2-carboxylate S-oxide

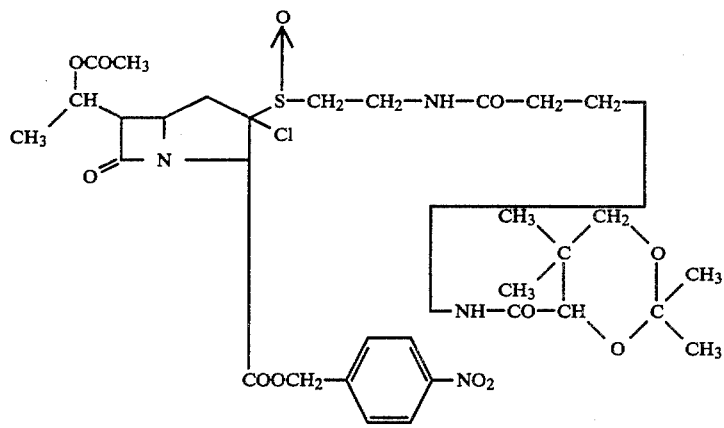

p-Nitrobenzyl 6-(1-acetoxyethyl)-3-isopropylidenepantetheinyl-7-oxo-1-azabicyclo[3.2.0]heptane-2-carboxylate (31 mg) was dissolved in a mixture of 1 ml of benzene and 1 ml of methylene chloride, and the solution was cooled to 0° C. Pyridine (16 μl) and 24 mg of iodobenzene dichloride were added, and the reaction was carried out at the same temperature for 2 hours. The reaction mixture was chromatographed on a column of 10 ml of silica gel using a 1:1 mixture of benzene and acetone as eluent. Active fractions which showed a UV absorbing spot at Rf 0.44 on a silica gel thin-layer chromatographic plate developed with the same solvent system as above were concentrated to dryness under reduced pressure to provide 15 mg of the captioned compound. This compound had the following properties.

IR Spectrum: $\nu_{max}^{CHCl_3}$ cm$^{-1}$: 1782 (β-lactam), 1740 (ester), 1665 (amide).

UV Spectrum: $\lambda_{max}^{CH2Cl2}$ nm(ε): 267 (10700).

NMR Spectrum (CDCl$_3$) δ

0.94 (3H, s,

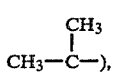), 1.01 (3H, s,

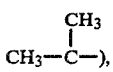), 1.24 (3H, d, J=7.0 Hz, C$\underline{H}_3$—CH),
1.38 (3H, s,

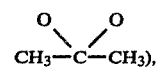), 1.41 (3H, s,

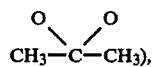), 2.04 (3H, s, CH$_3$CO),
2.10–2.50 (3H, m, C-4H, NH—CH$_2$—CH$_2$—CO),
2.70–3.90 (10H, m, C-4H, C-6H, NH—CH$_2$—CH$_2$—CO, S—CH$_2$—CH$_2$—NH, O—CH$_2$—C),
4.00 (1H, s,

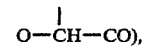), 4.08–4.45 (1H, m, C-5H),
4.97 (1H, s, C-2H),
5.18 (2H, s, C$\underline{H}_2$—Ar),
5.28–5.60 (1H, m, C-8H),
6.48 (1H, br, NH), 6.90 (1H, br, NH),
7.49 (2H, d, J=9.0 Hz, Ar—H),
8.15 (2H, d, J=9.0 Hz, Ar—$\underline{H}$).

Mass spectrum (FD): m/z: 743 (M$^{+1}$), 707 (m-Cl).

REFERENTIAL EXAMPLE 3

Production of p-nitrobenzyl 6-(1-acetoxyethyl)-3-isopropylidenepantetheinyl-7-oxo-1-azabicyclo[3.2.0]hept-2-ene-2-carboxylate S-oxide

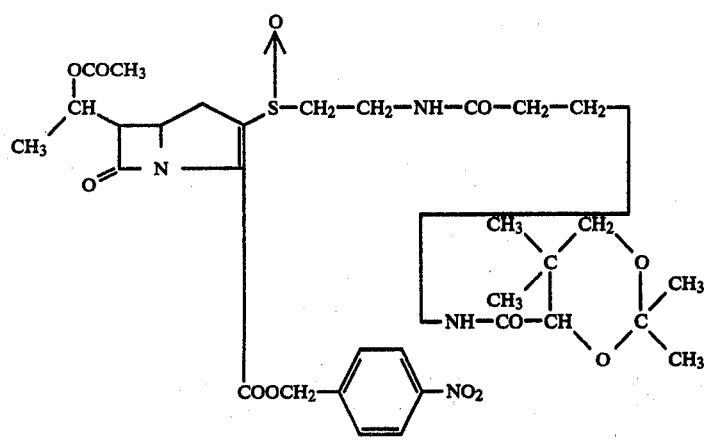

p-Nitrobenzyl 6-(1-acetoxyethyl)-3-chloro-3-isopropylidenepantetheinyl-7-oxo-1-azabicyclo[3.2.0]heptane-2-carboxylate S-oxide (7.9 mg) in 1.5 ml of benzene was mixed with 4 μl of triethylamine. The reaction was carried out at room temperature for 30 minutes. The reaction mixture was chromatographed on a column of 5 ml of silica gel using a 1:3 mixture of benzene and acetone as eluent. Active fractions which showed a UV absorbing spot at Rf 0.11 on a silica gel thin-layer chromatography plate developed with a 1:1 mixture of benzene and acetone were concentrated to dryness under reduced pressure to yield 5.7 mg of the captioned compound. This compound had the following properties:

IR Spectrum: $\nu_{max}^{CHCl_3}$ cm$^{-1}$: 1785 (β-lactam), 1735, 1710 (ester), 1660 (amide).

$\lambda_{max}^{CH_2Cl_2}$ nm(ε): 310 (7200), 269 (12600).

NMR Spectrum (CDCl$_3$): δ:

0.93 (3H, s,

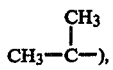

), 1.00 (3H, s,

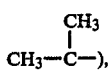

), 1.37 (3H, s,

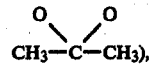

), 1.37 (3H, d, J=7.0 Hz, C$\underline{H}_3$—CH),
1.42 (3H, s,

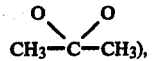

), 2.02 (3H, s, CH$_3$CO),
2.41 (2H, t, J=6.5 Hz, NH—CH$_2$—CH$_2$—CO),
2.80–3.90 (11H, m, C-4H$_2$, C-6H, N$\underline{H}$—CH$_2$—CH$_2$—CO, S—C$\underline{H}_2$—C$\underline{H}_2$—NH, O—CH$_2$—C̄),
4.02 (1H, s,

O—C̱H—CO), 4.20–4.55 (1H, m, C-5H),
5.10–5.40 (3H, m, C-8H, C$\underline{H}_2$—Ar),
6.54 (1H, br, NH),
6.93 (1H, br, NH),
7.58 (2H, d, J=8.5 Hz, Ar—$\underline{H}$),
8.17 (2H, d, J=8.5 Hz, Ar—$\underline{H}$).

REFERENTIAL EXAMPLE 4

Production of p-nitrobenzyl 6-(1-acetoxyethyl)-3-isopropylidenepantetheinyl-7-oxo-1-azabicyclo[3.2.0]hept-2-ene-2-carboxylate

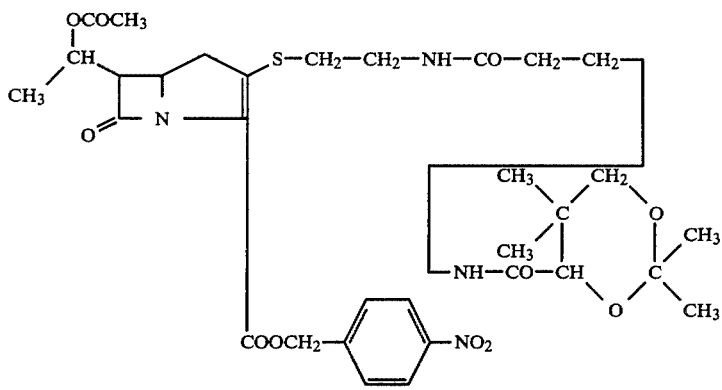

Ten mg of p-nitrobenzyl 6-(1-acetoxyethyl)-3-isopropylidenepantetheinyl-7-oxo-1-azabicyclo[3.2.0]hept-2-ene-2-carboxylate S-oxide (10 mg) was dissolved in 2 ml of benzene and mixed with 4 μl of tributylphosphine. The reaction was carried out at room temperature for 30 minutes. The solvent was evaporated off under reduced pressure. The residue was chromatographed on a column of silica gel with a 2:1 mixture of benzene and acetone as eluent. Active fractions which showed a UV absorbing spot at Rf 0.46 on a silica gel thin-layer chromatographic plate developed with a 1:1 mixture of benzene and acetone were collected and evaporated to dryness under reduced pressure to give 5.0 mg of the captioned compound. This compound had the following properties.

Specific rotation: $[\alpha]_D^{24}$ 35.4° (c=0.35, $CH_2Cl_2$).

IR Spectrum: $\nu_{max}^{CHCl_3}$ cm$^{-1}$: 1780 (β-lactam), 1735, 1700 (ester), 1660 (amide).

UV Spectrum $\lambda_{max}^{CH_2Cl_2}$ nm(ε): 317.5 (14600), 270.5 (12700).

NMR Spectrum (CDCl₃): δ:

0.95 (3H, s,

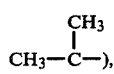

1.02 (3H, s,

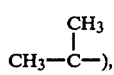

1.37 (3H, d, J=7.0 Hz, C$\underline{H}_3$—CH),
1.39 (3H, s,

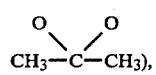

1.44 (3H, s,

2.03 (3H, s, CH₃CO), 2.42 (2H, t, J=6.5 Hz, NH—C$\underline{H}_2$—C$\underline{H}_2$—CO),
2.70–3.80 (11H, m, C-4H₂, C-6H, S—C$\underline{H}_2$—C$\underline{H}_2$—NH, NH—C$\underline{H}_2$—CH₂—CO, O—CH₂—C),
4.00 (1H, s,

4.10–4.45 (1H, m, C-5H),
5.00–5.40 (2H, m, C-8H, C$\underline{H}$H—Ar),
5.41 (1H, d, J=14.0 Hz, CH$\underline{H}$—Ar),
6.50 (1H, br, NH),
6.90 (1H, br, NH),
7.57 (2H, d, J=8.0 Hz, Ar—$\underline{H}$),
8.13 (2H, d, J=8.0 Hz, Ar—$\underline{H}$).

What we claim is:

1. A compound represented by the following formula

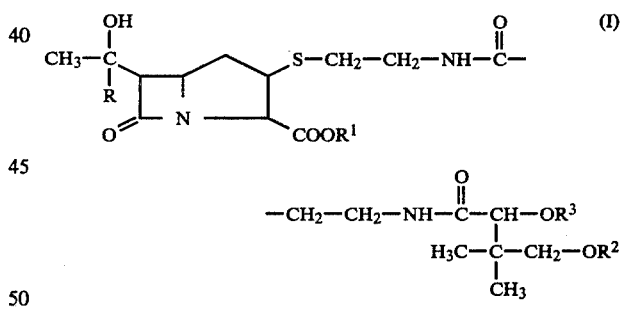

wherein
R represents a hydrogen atom or a methyl group,
R¹ represents a hydrogen atom or an ester residue, and
R² and R³ represent hydrogen atoms respectively, or taken together, a group of the formula $$\diagup^{R^4}_{C}\diagdown_{R^5}$$

in which each of R⁴ and R⁵ represents a hydrogen atom, a lower alkyl group or a phenyl group, or its salt.

2. The compound or its salt according to claim 1 wherein all of R, R¹, R² and R³ are hydrogen atoms.

3. The compound according to claim 1 wherein R, $R^2$ and $R^3$ are hydrogen atoms, and $R^1$ is an unsubstituted or substituted benzyl group.

4. The compound or its salt according to claim 1 wherein R is a methyl group and $R^1$, $R^2$ and $R^3$ are hydrogen atoms.

5. The compound according to claim 1 wherein R is a methyl group, $R^1$ is an unsubstituted or substituted benzyl group, and $R^2$ and $R^3$ are hydrogen atoms.

6. The compound according to claim 1 wherein $R^1$ is an unsubstituted or substituted benzyl group, and $R^2$ and $R^3$, taken together, form an isopropylidene group.

7. The salt according to any one of claims 1 to 6 which is a sodium salt.